US011529552B2

United States Patent
Aupetit et al.

(10) Patent No.: US 11,529,552 B2
(45) Date of Patent: Dec. 20, 2022

(54) SPORT DESIGN, TRACKING, AND COMMUNITY SYSTEM

(71) Applicant: Qatar Foundation for Education, Science and Community Development, Doha (QA)

(72) Inventors: Michael Jean-Marie Aupetit, Doha (QA); Khalid Kunji, Doha (QA)

(73) Assignee: QATAR FOUNDATION FOR EDUCATION, SCIENCE AND COMMUNITY DEVELOPMENT, Doha (QA)

(*) Notice: Subject to any disclaimer, the term of this patent is extended or adjusted under 35 U.S.C. 154(b) by 196 days.

(21) Appl. No.: 17/175,085

(22) Filed: Feb. 12, 2021

(65) Prior Publication Data

US 2021/0252370 A1    Aug. 19, 2021

Related U.S. Application Data

(60) Provisional application No. 62/976,516, filed on Feb. 14, 2020.

(51) Int. Cl.
    *A63B 71/06*    (2006.01)
    *A63B 43/00*    (2006.01)
    (Continued)

(52) U.S. Cl.
    CPC ...... *A63B 71/0622* (2013.01); *A63B 24/0021* (2013.01); *A63B 43/004* (2013.01); *H04W 4/029* (2018.02); *A63B 71/0605* (2013.01); *A63B 2024/0025* (2013.01); *A63B 2071/0625* (2013.01); *A63B 2071/0655* (2013.01); *A63B 2208/12* (2013.01); *A63B 2220/12* (2013.01); *A63B 2220/803* (2013.01); *A63B 2220/833* (2013.01); *A63B 2220/836* (2013.01); *A63B 2225/02* (2013.01); *A63B 2225/50* (2013.01);
(Continued)

(58) Field of Classification Search
USPC .......................................................... 473/6
See application file for complete search history.

(56) References Cited

U.S. PATENT DOCUMENTS 11,040,246 B2 *    6/2021   Black ................ A63B 24/0021
2018/0256078 A1 *    9/2018   Vaterlaus ............... G16H 20/30
(Continued)

*Primary Examiner* — Pierre E Elisca
(74) *Attorney, Agent, or Firm* — K&L Gates LLP

(57) ABSTRACT

The present disclosure provides a new and innovative system for sport design, tracking, and sharing. The system includes a set of wireless components in communication with a computing system. The computing system may include a graphical user interface, and at least in some instances, communicates over a network with an external system such as a social media platform. Through the graphical interface, a user may program rules to a sport into the wireless components. The user or users may perform the sport with the programmed wireless components, which analyze the actions performed according to the programmed rules. The analysis and other data collected by the wireless components may be reviewed by the users after playing the sport. Furthermore, the data collected and the rules programmed into the wireless components may be shared online to the external system for rating and ranking by an online community.

20 Claims, 3 Drawing Sheets

(51) Int. Cl.
*A63B 24/00* (2006.01)
*H04W 4/029* (2018.01)
*G09B 19/00* (2006.01)
*G06F 1/16* (2006.01)

(52) U.S. Cl.
CPC .......... *A63B 2225/74* (2020.08); *G06F 1/163* (2013.01); *G09B 19/0053* (2013.01)

(56) References Cited

U.S. PATENT DOCUMENTS

| | | | |
|---|---|---|---|
| 2019/0184230 A1* | 6/2019 | Lee | A63B 24/0062 |
| 2019/0240534 A1* | 8/2019 | Black | G06F 1/1692 |
| 2021/0205660 A1* | 7/2021 | Shavit | G06V 40/23 |

* cited by examiner

SPORT DESIGN, TRACKING, AND COMMUNITY SYSTEM

PRIORITY CLAIM

The present application claims priority to and the benefit of U.S. Provisional Application 62/976,516, filed Feb. 14, 2020, the entirety of which is herein incorporated by reference.

BACKGROUND

Worldwide there is a growing number of individuals suffering from depression, obesity and diabetes partly from a lack of physical activities and direct social interaction with their peers. Such habits can be particularly harmful to children and teenagers because they may be developing lifelong habits and they may be affecting their growth by having such habits. There is also a growing lack of interest in STEM studies among students, which affects the development of knowledge-based economies.

One way to encourage individuals, particularly children and teenagers, to participate in physical activity is video game systems that utilize sensors and motion-tracking technology to promote movement, such as the Nintendo Wii®. Such video game systems, however, require a screen as a reference point and thus limit users' movement. Additionally, such systems limit users to playing the games developed and released by professional game developers.

One way to help encourage individuals to take an interest in STEM studies are various systems, programs, and classes that enable individuals to build and/or create various projects. Typically, however, such systems, programs, and classes are sedentary and do not promote physical activity.

Accordingly, a need exists for a system that encourages individuals, particularly children and teenagers, to both engage in physical activity and take an interest in STEM studies.

SUMMARY

The present disclosure provides a new and innovative sport design system that aims to motivate users, particularly kids and teenagers, to participate in physical activity and in social interactions. The provided platform enables users to design and program the rules of a real sport they and their friends will play. Users get real time and aftermath sport analytics from when they play the sport based on external sensors, such as motion-tracking sensors. The sensors may be worn by the users, installed on or within the sporting equipment, and/or positioned on the field of play. Users may then share their sport rules and analytic data with other users worldwide through an external system, such as a social media platform. Users may interact on the external system to discuss designed sports and to design new sports.

In an example, a system includes sporting equipment and multiple wireless component in communication with a computing device. Each wireless component is a passive wireless component or an active wireless component. At least one of the wireless components is coupled to at least some of the sporting equipment. The computing device includes a display for displaying a graphical user interface, a memory, and a processor in communication with the memory. The processor receives instructions input via the graphical user interface and programs at least some of the wireless components according to the received instructions. The instructions input via the graphical user interface define rules to a game. Data from the wireless components is received by the processor. The processor may transmit commands to at least some of the wireless components. The received data may be presented on the display.

In an example, a system includes sporting equipment, a multiple wireless components in communication with a first computing device, and an external system in communication with the first computing device and with multiple second computing devices. Each wireless component is a passive wireless component or an active wireless component. At least one of the wireless components is coupled to at least some of the sporting equipment. The first computing device includes a display for displaying a graphical user interface, a memory, and a processor in communication with the memory. The processor receives instructions input via the graphical user interface and programs at least some of the wireless components according to the received instructions. The instructions input via the graphical user interface define rules to a game. Data from the wireless components is received by the processor. The processor may transmit commands to at least some of the wireless components. The received data may be presented on the display. The instructions input via the graphical user interface may be transmitted to the external system.

Additional features and advantages of the disclosed method and apparatus are described in, and will be apparent from, the following Detailed Description and the Figures. The features and advantages described herein are not all-inclusive and, in particular, many additional features and advantages will be apparent to one of ordinary skill in the art in view of the figures and description. Moreover, it should be noted that the language used in the specification has been principally selected for readability and instructional purposes, and not to limit the scope of the inventive subject matter.

DETAILED DESCRIPTION

Figure 1:
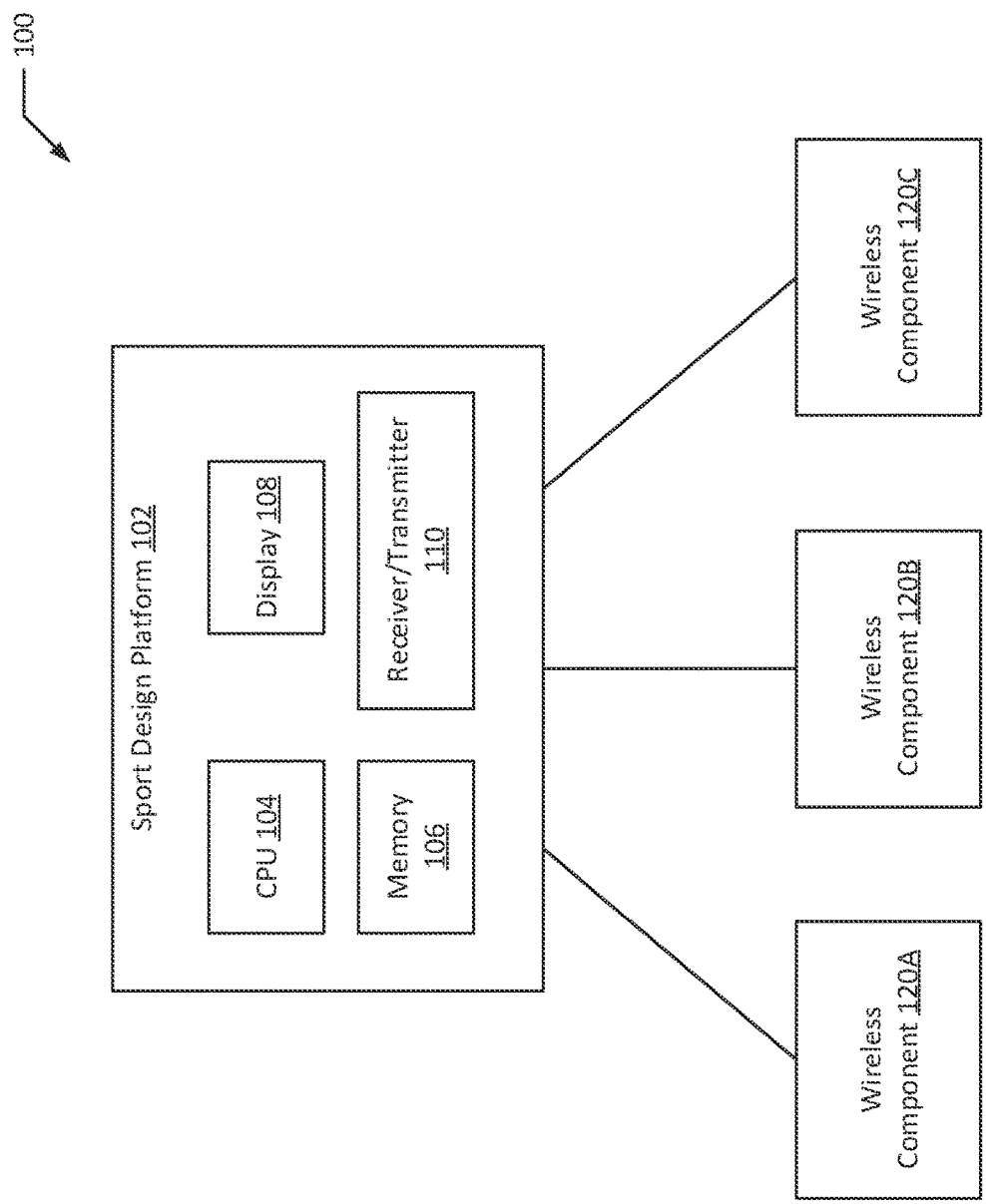
FIG. 1 illustrates a box diagram of an example system for sport design, according to an aspect of the present disclosure.

The present disclosure provides a new and innovative systems for sport design, tracking, and sharing. The provided system includes a set of wireless components, such as sensors and emitters, communicatively connected to a computing device and/or system. In at least some aspects, the computing system may have a graphical user interface. The computing system can be connected over a network (e.g., the Internet) to a social media platform or other remote systems. Through the graphical interface, a user (e.g., a child) may use a graphical programming interface to program rules into the wireless components. Once the wireless components are programmed with the customized rules, the user or users perform a physical activity (e.g., a sport) that is analyzed by the wireless components according to the programmed rules. The analysis and other data collected by the wireless components may be reviewed by the users in real-time or after the game is over and collection completes. Furthermore, the data collected and the rules programmed into the wireless components may be shared online to the social media platform and other remote systems for rating and ranking by an online community.

In an example embodiment of the provided system, a child or multiple children may decide the rules of their new game (e.g., a sport). The children may code their rules of the sports game into the wireless components using the graphical interface. In various aspects, the graphical interface may provide specific rules and building blocks that the children can select from based on the available wireless components. The wireless components may be used in a variety of ways for a game. For example, the children may wear the wireless components, may couple the wireless components with a piece of sporting equipment such as a ball, or may position the wireless components in a field of play. Once the programmed wireless components are in place, the children play the sports game based on their rules.

Activity is monitored by the wireless components according to the code as programmed previously. For example, the wireless components may monitor individuals' movements while playing the sport or may monitor movements of sporting equipment. Once the game has completed, the children may analyze the collected data through a graphical interface. The children may then upload the rules of their new sports game as well as the collected data onto an external system or server, such as a social media platform. Following the upload, other children may download these rules and play the same sport using their own sporting equipment, and upload the collected data from their sport session to the same external system or server. Eventually, the rules of the new sports game may be played by many different groups of children, garnering ratings and rankings in the process as viewed on the external system or server. In this way, the provided system encourages users, particularly children and teenagers, to perform physical activity by playing the sport that the users design.

The provided system may also help promote an interest in STEM studies among students by enabling individuals to design and code their own sports that they can then physically play. The provided system helps children and teenagers in particular benefit from learning basic programming and game design skills (e.g., STEM education, social science), doing physical activity (e.g., physical health) and socialization (e.g., mental health, negotiation, leadership) as per their own game rules (empowerment, imagination, responsibilities). Schools could benefit from the system to support STEM education and physical activities. In another example, the system could help foster the collective development of serious sport games directed to camps for children against obesity and diabetes. Additionally, by enabling users to share designed sport rules among a community, the provided system may help spread new sports for others to participate in.

In another example, the provided system could be used to help train athletes or other individuals. For instance, various equipment having wireless components can be programmed with rules for a specific training exercise. In such instances, the wireless components could track the athletes' or individuals' movements to quantify their performance in a training session and/or monitor their progress across multiple training sessions.

In another example, the provided system can be used for clinical physiotherapy for the elderly, individuals with special needs, or individuals that are rehabbing an injury. For instance, a physiotherapist could program specific physical activity rules into equipment having wireless components that is used for a patient's exercises, with the rules being tailored for the patient's capacities. In such instances, the provided system's wireless components could track the patient's movements to, for example, alert the patient that the patient is performing particular movements correctly or enable the physiotherapist to monitor the patient's progress or activity level. In one particular example, balls having wireless components that emit sounds could be used by visually impaired people to play a game or to exercise.

As used herein, sporting equipment refers to any suitable item of equipment that may be used for an activity, recreation, exercise, game, sport, etc. involving physical activity. For example, sporting equipment may refer to, but is not limited to, a ball (e.g., a basketball, football, baseball, soccer ball, tennis ball, racquetball, golf ball, lacrosse ball, dodgeball, kickball, foam ball, rubber ball, plastic ball, etc.), a puck, a bat, a stick (e.g., a hockey or lacrosse stick), a club (e.g., golf club), a racquet, a glove, a cone, hurdles, goal posts, netting, protective gear such as a helmet or pads, an exercise weight, a resistance band, or other suitable items of equipment used for an activity, recreation, exercise, game, sport, etc. involving physical activity.

FIG. 1 illustrates an example sport design system 100 for designing and performing a sport, according to an aspect of the present disclosure. The sport design system 100 includes a sport design platform 102. The sport design platform 102 is a computing device such as a computer, laptop, tablet, smartphone, etc. that includes a processor in communication with a memory 106. The processor may be a CPU 104, or any other similar device. The sport design platform 102 is in communication with multiple wireless components 120A, 120B, 120C. The sport design system 100 may include any quantity of wireless components 120A, 120B, 120C (e.g., 1, 2, 3, 7, 15, 30, etc.). In at least some aspects, the sport design platform 102 includes a receiver/transmitter 110 configured to receive wireless signals from, and transmit wireless signals to, the wireless components 120A, 120B, 120C. In other examples, the components of the sport design platform 102 may be combined, rearranged, removed, or provided on a separate device or server.

In various aspects, a wireless component 120A, 120B, or 120C may be worn by individuals. For example, a wireless component 120A, 120B, or 120C may be integrated into a wristband (e.g., a watch), an armband, or a headband, or may include an attachment mechanism (e.g., a clip) for attaching the wireless component 120A, 120B, or 120C to an individual's clothing. In various aspects, a wireless component 120A, 120B, or 120C may be coupled or integrated with, or installed within, an item of sporting equipment. For example, a wireless component 120A, 120B, or 120C may be installed inside a ball or attached to a bat. In various aspects, a wireless component 120A, 120B, or 120C may be positioned on a field of play. For example, a wireless component 120A, 120B, or 120C may be a standalone item placed at a boundary to the field of play or may be attached or integrated with an item of sporting equipment (e.g., a cone) that is positioned on the field of play.

In some aspects, a wireless component 120A, 120B, or 120C may be a passive component (e.g., a magnetic or passive RFID tag). In an example of such aspects, a passive wireless component 120A, 120B, 120C may trigger an action of another wireless component 120A, 120B, 120C passing nearby the passive wireless component 120A, 120B, 120C. In some aspects, a wireless component 120A, 120B, or 120C may be an active component (e.g., an active RFID tag) having its own power supply (e.g., a battery or solar panel). An active wireless component 120A, 120B, 120C, in some examples, may have its own memory and processor having internal logic. In some aspects, the memory and internal logic of the active wireless component 120A, 120B, 120C is sufficient only to transfer a signal from the wireless component 120A, 120B, 120C to the sport design platform 102 or to receive a signal from the sport design platform 102. In other aspects, the memory and internal logic of the active wireless component 120A, 120B, 120C enables the active wireless component 120A, 120B, 120C to receive, process, and act on information independently from the sport design platform 102. In either of these aspects, a user may program the internal logic of the active wireless component 120A, 120B, 120C using the sport design platform 102.

Aspects in which at least some of the wireless components 120A, 120B, 120C in the sport design system 100 receive, process, and act on information independently from the sport design platform 102 has the advantage of faster data processing over aspects in which the wireless components 120A, 120B, 120C do not. For instance, the parallelization of the wireless components 120A, 120B, 120C performing their own tasks locally eliminates the communication time of transmitting data to the sport design platform 102 and also frees up bandwidth at the sport design platform 102. The faster data processing enables the wireless components 120A, 120B, 120C to have quicker reaction times in response to collected data, which can contribute to users' enjoyment of their sports game or physical activity.

In some aspects, a wireless component 120A, 120B, or 120C may be a sensor that collects information (e.g., movement, position, speed, acceleration, temperature, light, sound, chemicals, etc.) and transforms that information into digital data. At least in some instances, the wireless component 120A, 120B, or 120C may transmit that digital data to the sport design platform 102. In at least one particular example, a wireless component 120A, 120B, or 120C may be a motion sensor that either detects that the wireless component 120A, 120B, or 120C itself has moved or that detects motion of another object across a line of sight of the wireless component 120A, 120B, or 120C. In some aspects, one or more of the wireless components 120A, 120B, 120C may be components of a positioning system (e.g., an indoor positioning system) that tracks the positioning of each of the wireless components 120A, 120B, 120C in the positioning system. In some examples, the sport design platform 102 may utilize GPS or another suitable positioning system. In some examples, the positioning system may be implemented by software executed by the CPU 104 of the sport design platform 102.

A wireless component 120A, 120B, or 120C may collect any suitably pertinent information to a sport being played or activity being performed or to an individual's physical activity during the time the individual is playing such sport or performing such activity. For example, the wireless component 120A, 120B, or 120C may track the individual's movements as the individual plays the sport to provide various metrics of the individual's physical activity, such as time of physical activity, heart rate, calories burned, steps taken, amount of intense exercise, or other suitable indicators metrics. In such an example, a wireless component 120A, 120B, or 120C may include an accelerometer. In another example, the wireless components 120A, 120B, or 120C may be positioned such that they are able to monitor when a ball or individual passes a boundary, when a ball makes contact with a surface, whether an object such as a cone is moved, whether one object is a threshold distance away from another object, or numerous other suitable actions that may occur in a sports game or other physical activities (e.g., a training session). The information, or data, may be provided to the sport design platform 102 in real-time (e.g., near contemporaneously with the information or data being received), at periodic intervals (e.g., every 30 seconds) during the sports game or physical activity, or after the sport session or physical activity is completed.

In some aspects, a wireless component 120A, 120B, or 120C may be an actuator that generates a signal, or alert, in response to the information it collects or in response to a command it receives from the sport design platform 102. For instance, the signal, or alert, that the wireless component 120A, 120B, or 120C generates may be a sound, a light, a vibration, etc. In such aspects, a wireless component 120A, 120B, or 120C may, for example, include a buzzer or an LED. It should be appreciated that a wireless component 120A, 120B, 120C can be a sensor, an actuator, or both a sensor and an actuator. In an example, a wireless component 120A, 120B, or 120C may emit a sound in response to detecting the motion of an individual moving past the wireless component 120A, 120B, or 120C, which may indicate that the individual is out of bounds based on the rules of the sport. In another example, when the sport design platform 102 detects via an indoor positioning system that a wireless component 120A, 120B, or 120C is at a particular position, such as a scoring region in the sports game, the sport design platform 102 may transmit a command to each of the wireless components 120A, 120B, 120C that are worn by individuals to cause each of the wireless components 120A, 120B, 120C to vibrate.

As described above, individuals may create their own rules for a sports game by programming, or providing instructions to, the sport design platform 102. To enable individuals to do so, in at least some aspects, the sport design platform 102 includes a display 108. An individual may interact with a graphical user interface (GUI) shown on the display 108 of the sport design platform 102 to input instructions, or rules, for a sport. Based on these rules, in some aspects, the processor programs the wireless components 120A, 120B, 120C that are in communication with the sport design platform 102 to perform certain actions in response to detecting, or sensing, certain information. In other aspects, the processor is programmed to take certain actions in response to the information it receives from the wireless components 120A, 120B, 120C. For example, in such other aspects, the processor may transmit a command to a wireless component 120A, 120B, or 120C to emit a sound in response to receiving data from the wireless component 120A, 120B, or 120C indicating that an object is a threshold distance away from the wireless component 120A, 120B, or 120C. In any of these aspects, an individual partakes in some level of programming via the sport design platform 102 so that the wireless components 120A, 120B, and 120C and the sport design platform 102 perform according to the programmed rules.

In some examples, the GUI shown on the display 108 may provide specific rules or building blocks that a user can select from to generate a sports game. In some instances, the specific rules or building blocks may be based on a particular experience level that a user selects. For example, a user with limited programming knowledge (e.g., a young child) may select a beginner experience level that provides the user with rules or building blocks having descriptive titles or names (e.g., "detect movement" or "emit sound") for actions to help the user complete the creation of a sports game. When the user selects a rule or building block with a descriptive title or name, the sport design platform 102 applies the corresponding programming language to the wireless component 120A, 120B, or 120C to which the descriptive rule or building block applies. In some instances, the specific rules or building blocks available to a user may be based on the wireless components 120A, 120B, 120C that are available for use. In such instances, two individuals using two different sport design platforms 102 might have different rules or building blocks depending on the wireless components 120A, 120B, 120C that each individual has.

The sport design platform 102 provides a user with flexibility to program rules with any level of complexity that the user desires. For example, the user may program a wireless component 120A, 120B, 120C to emit a sound after a predetermined amount of time has elapsed. In another example, the user may program a wireless component 120A, 120B, 120C to emit a first sound after a first predetermined amount of time has elapsed and to emit a second, different sound after a second, subsequent predetermined amount of time has elapsed. In another example, the user may program a wireless component 120A, 120B, 120C to emit a first sound upon the wireless component 120A, 120B, 120C being moved, to emit a second, different sound upon the wireless component 120A, 120B, 120C being located in a particular area on a field of play, and to emit a third, different sound after a predetermined amount of time has elapsed. The flexibility with which rules may be programmed using the sport design platform 102 provides an advantage over typical systems that provide users with limited rules with which to play a game, such as a system including a sensor that is programmed to perform only a single action in response to specific information.

Figure 2:
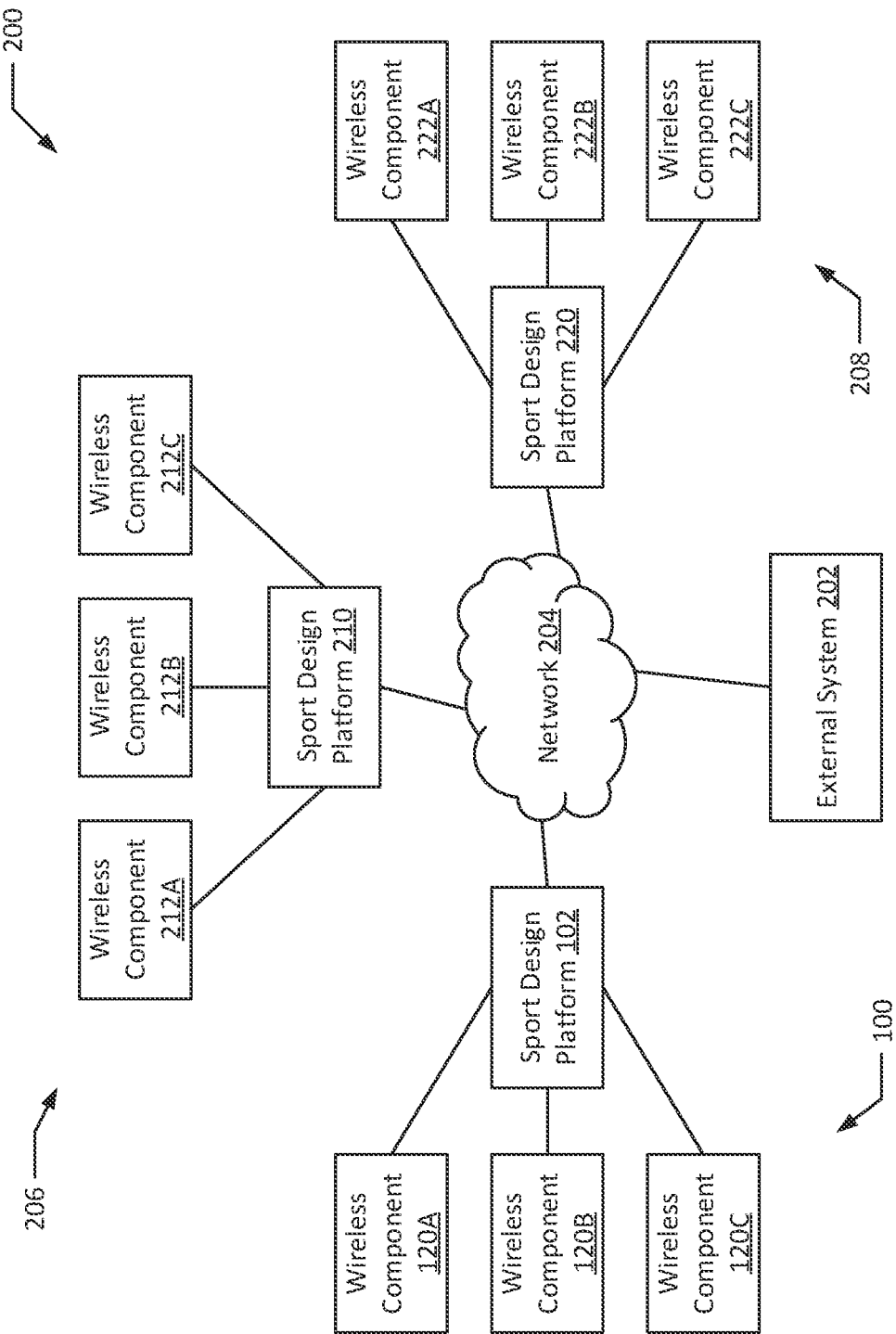
FIG. 2 illustrates a box diagram of an example system for sport design, tracking, and sharing, according to an aspect of the present disclosure.

As shown in the example system 200 of FIG. 2, in various aspects, the sport design system 100 (e.g., the sport design platform 102) may be in communication with an external system 202, such as over a network 204. The network 204 can include, for example, the Internet or some other data network, including, but not limited to, any suitable wide area network or local area network. In an example, the external system 202 is a social media platform. The external system 202 may include at least one processor in communication with a memory, and may be configured to receive, store, and transmit information. Multiple other sport design systems 206, 208 may be in communication with the external system 202, such as over the network 204. Though only the two sport design systems 206 and 208 are illustrated, any quantity of other sport design systems 206, 208 may be in communication with the external system 202. The sport design system 206 includes its own sport design platform 210 that may be in communication with its own wireless components 212A, 212B, 212C. The sport design system 208 includes its own sport design platform 220 that may be in communication with its own wireless components 222A, 222B, 222C. In some aspects, the external system 202 is a closed system dedicated solely to users of a sport design system 100, 206, or 208. For example, users may need login information that they obtain from purchasing a sport design system 100, 206, or 208 to access the external system 202. In other aspects, the external system 202 may be a system that is open to all individuals, or to all individuals that create login information.

The external system 202 enables individuals to share information with respect to the sports games that they design. For example, an individual using the sport design system 100 may upload the rules or programming language of the sports game the individual created to the external system 202 in order to share the rules or programming language with other individuals. For instance, an individual using the sport design system 206 may download these rules or programming language so that the individual may play the sports game with the sport design platform 210 and the wireless components 212A, 212B, and 212C. Individuals may also communicate messages through the external system 202. In some aspects, individuals may upload to the external system 202 their statistics from playing a sport they created or from playing a sport that they downloaded. In this way, individuals may then compete to outperform the uploaded statistics. The external system 202 may, in some aspects, track how often a particular set of sport rules are downloaded and played. In this way, individuals may compete to create a sport that is played by the most people.

In one aspect of the present disclosure, individuals in different geographical locations (e.g., different cities, states, regions, countries, etc.) can compete against one another at the same time in the same sport using their respective sport design systems 100, 206, 208. Any suitable quantity of sport design systems 100, 206, 208 may be in communication with one another to enable the individuals in different geographical locations to compete in the same sport at the same time. For example, information collected by a wireless component 120A, 120B, or 120C in the sport design system 100 located in Chicago, Ill. may cause a wireless component 212A, 212B, or 212C in the sport design system 210 located in Doha, Qatar to perform an action, such as emit a sound or a light. In this way, an indication is made to the individual(s) playing the sport with the sport design system 210 that the individual(s) playing the sport with the sport design system 100 scored a point, lost a point, ended the game, etc. Information collected by a wireless component 120A, 120B, or 120C may be transmitted to the sport design platform 102, then to the sport design platform 210 over the network 204, and the sport design platform 210 may cause a wireless component 212A, 212B, or 212C to perform the action. In some aspects, the information may be routed through the external system 202 between the sport design platform 102 and the sport design platform 210. In some aspects, the sport design systems 100, 206, and 208 all exchange information collected by their respective wireless components with each other.

Figure 3:
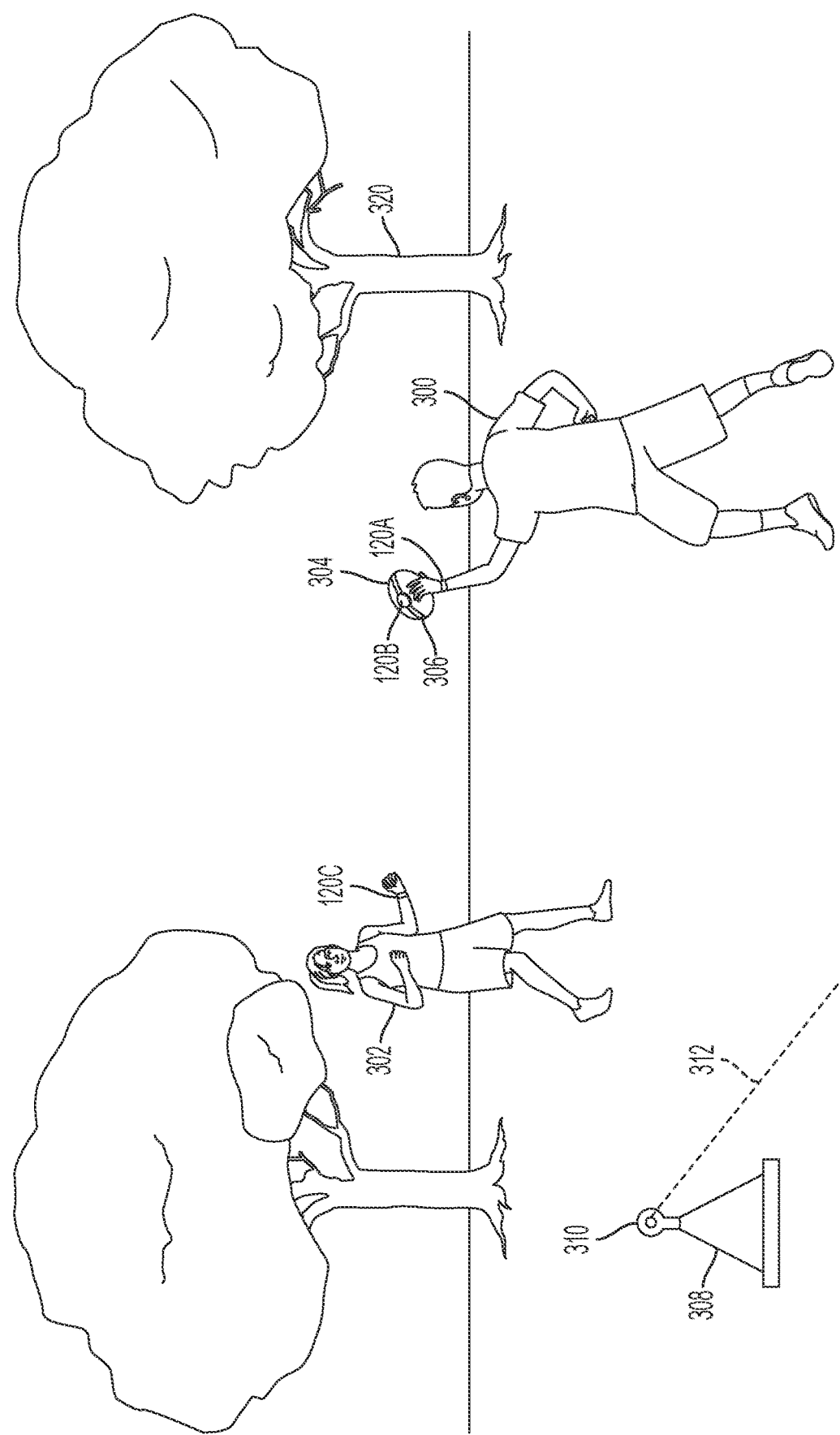
FIG. 3 illustrates individuals playing a sport using the provided system for sport design, according to an aspect of the present disclosure.

FIG. 3 illustrates a snapshot of an example sports game being played between the individual 300 and the individual 302 using the sports design system 100. The individual 300 is wearing a wristband integrated with the wireless component 120A. Similarly, the individual 302 is wearing a wristband integrated with the wireless component 120B. The individual 300 is shown running while holding a ball 304. The wireless component 120C is coupled to the ball 304 by a strap 306. In this example sports game, the individual 300 wins the game if the individual 300 brings the ball 304 to the tree 320. The sport design platform 102 may track a position of the wireless component 120B (e.g., with a positioning system) to determine when the wireless component 120B is positioned at the tree 320. In this example, once the sport design platform 102 determines that the wireless component 120 is positioned at the tree 320, the sport design platform 102 will transmit a command to the wireless component 120B that causes the wireless component 120B to light up and emit a sound, which indicates to the individual 300 and the individual 302 that the game has been won.

Also illustrated is a cone 308 having a wireless component 310. The wireless component 310 may be attached to, or integrated with, the cone 308. In this example, the wireless component 310 is a motion sensor that detects motion across its line of sight 312. The cone 308 and the wireless component 310 are positioned on the field of play such that the line of sight 312 of the wireless component 310 defines a boundary line for the game. In this example sports game, if the individual 300 runs past this boundary line, the individual 300 is out of bounds and has to give up the ball 304 according to the example sports game's rules. To indicate that the individual 300 is out of bounds, when the wireless component 310 detects movement across its line of sight 312 the wireless component 310 transmits a signal to the sport design platform 102, and in response, the sport design platform 102 transmits a command to the wireless components 120A and 120C that causes each of them to vibrate. In this way, the individual 300 and the individual 302 are alerted by the vibration that the individual 300 crossed over the boundary line. All of these described actions of the wireless components 120A, 120B, 120C, and 310 and the sport design platform 102 can be programmed by the individual 300 and/or the individual 302 using the sport design platform 102.

Without further elaboration, it is believed that one skilled in the art can use the preceding description to utilize the claimed inventions to their fullest extent. The examples and aspects disclosed herein are to be construed as merely illustrative and not a limitation of the scope of the present disclosure in any way. It will be apparent to those having skill in the art that changes may be made to the details of the above-described examples without departing from the underlying principles discussed. In other words, various modifications and improvements of the examples specifically disclosed in the description above are within the scope of the appended claims. For instance, any suitable combination of features of the various examples described is contemplated.

The invention is claimed as follows:

1. A sport design system comprising:
   sporting equipment;
   a plurality of wireless components in communication with a computing device, wherein each wireless component is a passive wireless component or an active wireless component; and
   the computing device including:
     a display for displaying a graphical user interface;
     a memory; and
     a processor in communication with the memory, the processor configured to:
       receive instructions input via the graphical user interface,
       program at least some of the plurality of wireless components according to the received instructions,
       receive data from at least some of the plurality of wireless components,
       transmit commands to at least some of the plurality of wireless components, and
       present the received data on the display,
   wherein the instructions input via the graphical user interface define rules to a physical activity, and
   wherein at least one of the plurality of wireless components is coupled to at least some of the sporting equipment.

2. The sport design system of claim 1, wherein the memory is a first memory and the processor is a first processor, and wherein an active wireless component includes a second processor in communication with a second memory, the second processor being configured to receive information and generate an alert based on the received information.

3. The sport design system of claim 1, wherein at least one of the plurality of wireless components is installed within an item of the sporting equipment.

4. The sport design system of claim 3, wherein the item of the sporting equipment is a ball.

5. The sport design system of claim 1, wherein at least one of the plurality of wireless components is configured to be worn by an individual participating in the physical activity.

6. The sport design system of claim 5, wherein the at least one of the plurality of wireless components configured to be worn by the individual is configured to track movements of the individual.

7. The sport design system of claim 1, wherein at least one of the plurality of wireless components is positioned on a field of play for the physical activity.

8. The sport design system of claim 1, wherein at least one of the plurality of wireless components is configured to emit a sound, a light, or a vibration.

9. The sport design system of claim 1, wherein one of the plurality of wireless components is coupled to or installed within an item of the sporting equipment, wherein one of the plurality of wireless components is configured to be worn by an individual participating in the physical activity, and wherein one of the plurality of wireless components is positioned on a field of play for the physical activity.

10. The sport design system of claim 1, wherein at least one of the plurality of wireless components is a sensor.

11. The sport design system of claim 10, wherein the sensor is configured to detect motion.

12. The sport design system of claim 1, wherein the instructions include one or more predetermined rules.

13. The sport design system of claim 1, wherein the processor is configured to receive the data from the plurality of wireless components contemporaneously with the physical activity being performed.

14. The sport design system of claim 1, wherein the processor is further configured to determine a positioning of each of the plurality of wireless components within an area of play.

15. The sport design system of claim 14, wherein the positioning of each of the plurality of wireless components is determined via an indoor positioning system.

16. A sport design system comprising:
    sporting equipment;
    a plurality of wireless components in communication with a first computing device, wherein each wireless component is a passive wireless component or an active wireless component;
    an external system in communication with the first computing device and with a plurality of second computing devices; and
    the first computing device including:
      a display for displaying a graphical user interface;
      a memory; and
      a processor in communication with the memory, the processor configured to:
        receive instructions input via the graphical user interface,
        program at least some of the plurality of wireless components according to the received instructions,
        receive data from at least some of the plurality of wireless components,
        transmit commands to at least some of the plurality of wireless components,
        present the received data on the display, and transmit the received instructions to the external system, wherein the instructions input via the graphical user interface define rules to a physical activity, and wherein at least one of the plurality of wireless components is coupled to at least some of the sporting equipment.

17. The sport design system of claim 16, wherein the plurality of wireless components are a first plurality of wireless components, the memory is a first memory, and the processor is a second processor, wherein each of the plurality of second computing devices includes a second memory in communication with a second processor, the second processor configured to:

receive the instructions from the external system; and program a second plurality of wireless components according to the instructions.

18. The sport design system of claim 17, configured such that data received by the first processor from the first plurality of wireless components causes at least one of the second plurality of wireless components to perform an action.

19. The sport design system of claim 18, wherein the first plurality of wireless components are in a different geographical location than the second plurality of wireless components.

20. The sport design system of claim 16, configured such that the first computing device may transmit communications to, and receive communications from, the plurality of second computing devices.

* * * * *